United States Patent [19]

Jaselskis et al.

[11] Patent Number: 5,952,561
[45] Date of Patent: Sep. 14, 1999

[54] REAL TIME ASPHALT PAVEMENT QUALITY SENSOR USING A DIFFERENTIAL APPROACH

[75] Inventors: Edward J. Jaselskis, Ames; Hsiu Han, West Des Moines, both of Iowa; Jonas Grigas, Vilnus, Lithuania

[73] Assignee: Iowa State University Research Foundation, Inc., Ames, Iowa

[21] Appl. No.: 08/971,081

[22] Filed: Nov. 14, 1997

Related U.S. Application Data

[60] Provisional application No. 60/040,840, Mar. 19, 1997.

[51] Int. Cl.⁶ ..................................................... G01N 3/00
[52] U.S. Cl. .................................................................. 73/78
[58] Field of Search ..................................... 73/866, 32 R, 73/78, 818, 823, 803, 84, 146, 81, 82; 250/341.8, 358.1; 324/637, 639, 642, 658, 663; 404/84.05, 122, 101

[56] References Cited

U.S. PATENT DOCUMENTS

| | | |
|---|---|---|
| 3,444,727 | 5/1969 | Bourdin et al. ............................. 73/78 |
| 4,658,639 | 4/1987 | Arnberg ...................................... 73/84 |
| 5,177,415 | 1/1993 | Quibel et al. . |
| 5,336,019 | 8/1994 | Hollon et al. ............................. 404/72 |
| 5,494,373 | 2/1996 | Amon ........................................ 404/74 |
| 5,507,593 | 4/1996 | Hollon et al. ........................... 404/122 |
| 5,581,191 | 12/1996 | Yamaguchi ............................. 324/637 |

OTHER PUBLICATIONS

Richard C. Ransom, P.E. and James T. Kunz, P.E., Nondestructive Detection of Voids Beneath Pavement, Jan. 1986, pp. 54–55, Public Works.

Craig A. Rodeick, Roadbed Void Detection by Ground Penetrating Radar, Jun. 1984, pp. 60–61, Highway & Heavy Construction.

Richard DeMeis, Radar Traps Road Flaws, Apr. 1994, pp. 22–23, Aerospace America.

Andrew J. Gisi, P.E., In–Depth Look at Concrete Pavement Rehabilitation, Aug. 1987, pp. 75–77, Public Works.

Jacob Greenstein, M.ASCE, Use of NDT and Pocket Computers in Pavement Evaluation, May 1985, pp. 258–267, Journal of Transportation Engineering.

New Tool for Nondestructive Thickness Measurements, Jan. 1995, pp. 53–54, Public Works.

James J. Pantina, Nondestructive Testing Cuts Runway Rehab Costs, Nov. 1983, pp. 43–45, Civil Engineering/ASCE.

Ground–Penetrating Radar Identifies Pavement Segments, Jan. 1991, pp. 66–67, Public Works.

Carla Juliani, Rating Runways, Oct. 1993, p. 14, ASTM Standardization News.

Gilbert Y. Baladi, NDT Methods of Pavement Evaluation, May 1984, pp. 36–37, ASTM Standardization News.

(List continued on next page.)

Primary Examiner—Robert Raevis
Attorney, Agent, or Firm—Zarley, McKee, Thomte, Voorhees & Sease

[57] ABSTRACT

A real time differential asphalt pavement quality sensor of the present invention is adapted to measure asphalt density in real time using a differential approach. Two sensors, one in the front of a roller and another behind the roller, measure reflected signals from the asphalt. The difference between the reflected signals provides an indication of the optimal compaction and density of the asphalt pavement. The invention looks at the change in variance over successive passes to determine when the optimal level of compaction has been reached.

18 Claims, 7 Drawing Sheets

OTHER PUBLICATIONS

Sandra L. Houston and Rohan Perera, Impact of Natural Site Variability on Nondestructive Test Deflection Basins, Sep./Oct. 1991, pp. 550–565, Journal of Transportation Engineering, vol. 117, No. 5.

Kevin Black and Peter Kopac, The Application of Ground–Penetrating Radar in Highway Engineering, Dec. 1992, pp. 96–103, Public Roads.

David J. Elton and Milten E. Harr, Nondestructive Pavement Evaluation Method, Jan. 1988, pp. 76–93, Journal of Transportation Engineering, vol. 114, No. 1.

Jacob Uzan and Robert L. Lytton, Experiment Design Approach to Nondestructive Testing of Pavements, Sep. 1989, pp. 504–521, Journal of Transportation Engineering, vol. 115, No. 5.

William N. Houston, Michael S. Mamlouck and Rohan W.S. Perera, Laboratory Versus Nonsdestructive Testing for Pavement Design, Mar./Apr. 1992, pp. 206–223, Journal of Transportation Engineering, vol. 118, No. 2.

Fredrich W. Jung, Nondestructive Testing: Interpretation of Deflection Bowl for Falling Weight Deflectometer Tests on Flexible Pavements, 1989, pp. 333–343, Journal of Testing and Evaluation.

Sasan Bakhitiari, Nasar Qaddoumi, Stoyan I. Ganchev and Reza Zoughi, Microwave Noncontact Examination of Disbond and Thickness Variation in Stratified Composite Media, Mar. 1994, pp. 389–395, IEEE Transactions on Microwave Theory and Techniques, vol. 42, No. 3.

Nachappa Gopalsami, Sasan Bakhtiari, Stephen L. Dieckman, Aposolos C. Raptis and Matthew J. Lepper, Millimeter–Wave Imaging for Nondestructive Evaluation of Materials, Mar. 1994, pp. 412–415, Materials Evaluation.

Reza Zoughi, Microwave and Millimeter Nondestructive Testing: A Succinct Introduction, Apr. 1995, pp. 461–462, Materials Evaluation.

Stoyan I. Ganchev, Robert J. Runser, Nasser Qaddoumi, Emarit Ranu and Gary Carriveau, Microwave Nondestructive Evaluation of Thick Sandwich Composites, Apr. 1995, pp. 463–467, Materials Evaluation.

W. Su, O.A. Hazim, Imad L. Al–Qadi and S.M. Riad, Permittivity of Portland Cement Concrete at Low RF Frequencies, Apr. 1994, pp. 496–502, Materials Evaluation.

R. Zoughi, G.L. Cone and P.S. Nowak, Microwave Nondestructive Detection of Rebars in Concrete Slabs, Nov. 1991, pp. 1385–1388, Materials Evaluation.

Udaya B. Halabe, Arash Sotoodehnia, Kenneth R. Maser and Eduardo A. Kausel, Modeling the Electromagnetic Properties of Concrete, Nov./Dec. 1993, pp. 552–563, ACI Materials Journal.

Chin–Yung Yeh, E. Ranu and Reza Zoughi, A Novel Microwave Method for Surface Crack Detection Using Higher Order Waveguide Modes, Jun. 1994, pp. 676–681, Materials Evaluation.

M. Bramanti and E. Salerno, Electromagnetic Techniques for Nondestructive Testing of Dielectric Materials: Diffraction Tomography, 1992, pp. 233–240, Journal of Microwave Power and Electromagnetic Energy, vol. 27, No. 4.

Reza Zoughi, Sheila D. Gray and Paul S. Nowak, Microwave Nondestructive Estimation of Cement Paste Compressive Strength, Jan./Feb. 1995, pp. 64–70, ACI Materials Journal.

Murray Parkinson, David Whitehead and John Wilson, Crossed Horizontal Dipoles Configures as Top–loaded Vertical Dipoles Transmitting High–frequency Radiation in the Ground Plane, Feb. 1993, pp. 585–586, Rev. Scl. Instrum. vol. 64, No. 2.

M. Bramanti and E. Salerno, Experiments on Some Particular Permittivity Sensors in Nondestructive Testing of Dielectric Materials, 1992, pp. 209–216, Journal of Microwave Power and Electromagnetic Energy, vol. 27, No. 4.

R. Zoughi and M. Lujan, Nondestructive Microwave Thickness Measurements of Dielectric Slabs, Sep. 1990, pp. 1100–1105, Materials Evaluation.

Milan Beres, Jr. and F.P. Haeni, Application of Ground–Penetrating–Radar Methods in Hydrogeologic Studies, May/Jun. 1991, pp. 375–386, Ground Water, vol. 29, No. 3.

Derald G. Smith and Harry M. Jol, Ground–penetrating Radar Investigation of a Lake Bonneville Delta, Provo Level, Brigham City, Utah, Dec. 1992, pp. 1083–1086, Geology, vol. 20.

Brian R. Pratt and Andrew D. Miall, Anatomy of a Bioclastic Grainstone Megashoal (Middle Silurian, southern Ontario) Revealed by Ground–Penetrating Radar, Mar. 1993, pp. 223–226, Geology, vol. 21.

Donald J. Lawrence and Peter C. Smith, Evaluation of HF Ground–Wave Radar on the East Coast of Canada, 1986, pp. 246–250, IEEE Journal of Oceanic Engineering, vol. OE–11, No. 2.

Ken J. Hickey, Eric W. Gill, James A. Helbig and John Walsh, Measurement of Ocean Surface Currents Using a Long–Range, High Frequency Ground Wave Radar, 1994, pp. 549–554 IEEE Journal of Oceanic Engineering, vol. 19, No. 4.

Tsuneo Imai, Toshihiko Sakayama and Takashi Kanemori, Use of Ground–Probing Radar and Resistivity Surveys for Archaeological Investigations, Feb. 1987, pp. 137–150, Geophysics, vol. 52, No. 2.

C.J. Vaughan, Ground–Penetrating Radar Surveys Used in Archaeological Investigations, Mar. 1986, pp. 595–604, Geophysics, vol. 51, No. 3.

Dean Goodman, Ground–Penetrating Radar Simulation in Engineering and Archaeology, Feb. 1994, Geophysics, vol. 59, No. 2.

John Walsh, Barry J. Dawe and Satish K. Srivastava, Remote Sensing of Icebergs by Ground–Wave Doppler Radar, Apr. 1986, pp. 276–284, IEEE Journal of Oceanic Engineering, vol. OE–11, No. 2.

Rafaat Khan, Brian Gamberg, Desmond Power, John Walsh, Barry Dawe, Wayne Pearson and Dave Millan, Target Detection and Tracking with a High Frequency Ground Wave Radar, Oct. 1994, IEEE Journal of Oceanic Engineering, vol. 19, No. 4.

Jame E. Kovas, Survey Applications of Ground–Penetrating Radar, 1991, pp. 144–148, Surveying and Land Information Systems, vol. 51, No. 3.

Jun Cai and George A. McMechan, Ray–Based Synthesis of Bistatic Ground–Penetrating Radar Profiles, 1995, pp. 87–96, Geophysics, vol. 60, No. 1.

Kathleen L. Virga and Yahya Rahmat–Samii, RCS Characterization of a Finite Ground Plane with Perforated Apertures: Simulations and Measurements, Nov. 1994, IEEE Transactions on Antennas and Propagation, vol. 42, No. 11.

Elizabeth Fisher, George A McMechan and A. Peter Annan, Acquisition and Processing of Wide–Aperture Ground–Penetrating Radar Data, Mar. 1992, Geophysics, vol. 57, No. 3.

Sun F. Shih and Don L. Myhre, Ground–Penetrating Radar for Salt–Affected Soil Assessment, Mar./Apr. 1994, pp. 322–333, Journal of Irrigation and Drainage Engineering, vol. 120, No. 2.

Elizabeth Fisher, George A. McMechan, A. Peter Annan and Steve W. Cosway, Examples of Reverse–Time Migration of Single–Channel Ground–Penetrating Radar Profiles, Apr. 1992, pp. 577–586, Geophysics, vol. 57, No. 4.

Fred L. Graf, Using Ground–Penetrating Radar to Pinpoint Pipeline Leaks, Apr. 1990, pp. 27–29, MP/Coatings & Linings.

Chun–Lok Lau, Tom Scullion, and Paul Chan, Jun. 1992, pp. 277–283, Geological Survey of Finland, Special Paper 16.

Trans Tech Systems, Inc., Dec. 1996, Testing and Trial Deployment of a Cost Effective and Real Time Asphalt Quality Inicator System, IDEA Program Report . . . Stage 1.

Solving for Voids Percentage, Real Density and Bulk Density, p. 73, Plant Notebook, Process Engineering.

REAL TIME ASPHALT PAVEMENT QUALITY SENSOR USING A DIFFERENTIAL APPROACH

CROSS REFERENCE TO RELATED APPLICATION

This application claims priority under 35 U.S.C. § 120 of co-pending, commonly owned U.S. provisional application Ser. No. 60/040,840 filed Mar. 19, 1997, entitled REAL TIME ASPHALT PAVEMENT QUALITY SENSOR.

BACKGROUND OF THE INVENTION

1. Field of the Invention

The present invention relates to asphalt pavement. More particularly, though not exclusively, the present invention relates to an apparatus and method for determining the quality of asphalt pavement in real time.

2. Problems in the Art

In order to rebuild and pave existing roads or highways that show signs of cracking and significant deterioration, or when building new roads or highways, it is important to effectively control the paving process. In the construction of roads, highways, or parking lots and the like using asphalt pavement, various factors affect the quality of the resulting asphalt surface. These factors include the proper mix of asphalt components and the proper compaction of the asphalt.

Hot asphalt mix has three components including aggregate, asphalt cement, and air voids. The force from a load on the pavement is transmitted through the pavement by interlocking contact between the aggregate particles. Friction at these contact points gives the asphalt pavement its stability. The asphalt cement binds the aggregate particles together after they have been compacted and the asphalt cooled. Air voids formed in the hot asphalt mix make up approximately 15% of the volume of the hot mix. Proper compaction (described below) reduces this percentage to about 5%.

After the hot asphalt mix is laid by the paver, it is compacted using one or more types of rollers. A first type of roller is a break down roller or vibratory roller. This is the first roller that is typically used and provides most of the compaction. A vibratory roller has one or two steel drums with rotating weights which vibrate the drums creating a dynamic force that adds to the dead weight of the roller and increases the compacting force. A second type of roller is a rubber tired roller or pneumatic roller which includes a number of rubber tires staggered to provide a complete coverage. The rubber tired roller kneads the surface and closes the pores formed on the top surface of the asphalt. A third type of roller is the finish roller which is used last to get rid of any creases formed by one of the previous rollers.

Many individuals are involved in producing a quality asphalt pavement (e.g., mix specifier, hot mix plant operator, quality assurance/quality control inspector, asphalt laying operator, and roller operator), but the roller operator's skill ultimately determines the final quality of the compacted mat, which directly relates to its density. Only a carefully planned rolling pattern gives the uniformity and desired density. The roller can achieve proper compaction only by monitoring the asphalt density in real time. An under-compacted asphalt mat is permeable to air and water, which shortens the pavement life. In addition, there will be too many air voids which makes the asphalt pavement less stable since the number of inter-particle contact points is reduced and it is more susceptible to freeze-thaw conditions. On the other hand, unnecessary over-compaction will crush the aggregate which will lead to a reduction of air void content, which, in turn, can make the pavement susceptible to permanent deformation. If the pavement is under-compacted or over-compacted, the paving contractor typically gets penalized. It is therefore very important to achieve the proper level of compaction.

Extensive effort has been devoted in the past to the nondestructive evaluation (NDE) of asphalt density characteristics. Nuclear density gauges, for example, have been used for several years to measure the bulk density of hot asphalt mixtures quickly and nondestructively. Some nuclear density gauges have even been attached to rollers to continuously measure density during the rolling operation. Troxler Electronic Laboratories, Inc., a manufacturer of such devices, has recently developed a new, surface moisture density gauge using a gamma ray backscattering approach that can be used in the field during the paving operation and provide results within seconds to minutes. These devices seem promising but have their limitations. For example, these devices require several minutes to obtain an accurate density measurement making it difficult to implement in real time on a continuous basis. Research has shown that there is significant variability of density test results between the nuclear density gauge and standard core sample approach. The variability of density tests is lower with core measurements than with nuclear density measurements. Because of this, some core samples need to be taken to ensure that an acceptable density is obtained. Furthermore, this technique requires measurements at discrete locations and does not readily lend itself to performing continuous density measurements on a moving roller. In addition, nuclear density gauges involve the use of ionizing radiation which requires safety precautions, certification of equipment, etc.

Ground-penetrating radar (GPR) is a promising NDE technique that has possibilities for measuring asphalt density in real time during the rolling operation. However, extended sensor calibrations are required for producing meaningful results. Ground-penetrating radar has been used extensively for NDE testing in many applications (e.g., oil and coal exploration, location of subsurface utilities, and detailed surveys to locate small voids or cracks in pavement). Ground-penetrating radar is also being used to determine the thickness and moisture content of asphalt pavement. Geophysical Survey Systems, Inc. (GSSI) has developed a high-speed radar for pavement structure evaluation including mapping asphalt thickness overlays, locating voids and large-scale structural problems, and checking the quality of the thickness of new asphalt concrete pavements. To date, GSSI has not developed a GPR unit that determines asphalt pavement density during the compaction process in real time. Computer programs exist which determine the density and water (or other fluid) content of the various layers within a multilayer system, using conventional GPR to obtain digitized images of a reflected radar signal from a multilayer pavement system. Such a system is not focused on determining the density of asphalt pavement during the rolling process; but, such correlations could theoretically be developed. Other prior art GPR systems include micropower impulse radar (MIR).

Another prior art method of testing asphalt densities involves the use of capacitance energy dissipation (CED) equipment. The CED method measures actual air voids based on the decay rate of energy stored in the asphalt segment when pulsed and compared to the decay rate of a reference capacitor with a known decay rate. CED involves placing a plate on the asphalt and charging it up while looking at the rate of dissipation of the charge. Various "correction factors" are required with this approach. The CED approach also requires stationary contact with the pavement surface. In addition, a temperature correction must be used since the results from a CED device vary depending on the temperature. Also since the plate makes contact with the pavement, it will have to be periodically cleaned.

One major problem with all prior art density testing techniques involves errors from variations in temperature, binder mix, and the aggregate. In other words, a prior art gauge may be calibrated for one binder for one temperature, etc. but then may be used to test asphalt using different binders, aggregates or at different temperatures. As a result, the user must recalibrate the gauge to correct for these variables to ensure an accurate reading.

The following references describe the prior art in detail and are incorporated by reference herein:

Al-Qadi, I. L., Ghodhaonkar, D. K., and Varadan, V, K., 1991. Effect Of Moisture On Asphaltic Concrete At Microwave Frequencies, IEEE Trans. Geoscience & Remote Sensing, Vol. 29, 710–717.

Alongi, A. V., and A. J. Alongi. Subsurface Inspection Radar. U.S. Pat. No. 4,698,634, Oct. 6, 1985.

"America's Highways Accelerating the Search for Innovation," Transportation Research Board, National Research Council, Special Report 202, Washington, D.C., Strategic Transportation Research Study: Highways.

Anderson, D. A., D. W. Christensen, H. U. Bahia, R. Dongre, M. G. Sharma, C. E. Antle, and J. Button. *Binder Characterization and Evaluation Volume 3: Physical Characterization*. Strategic Highway Research Program, SHRP-A-369, National Research Council, Washington, D.C. 1994.

Burati, J. L. Jr., and G. B. Elzoghbi. *Correlation of Nuclear Density Results with Core Densities*. Transportation Research Board, Transportation Research Record 1126, 1987.

Coon, J. B., and C. J. Schafers. Earth Probing Radar System. Conoco Inc., U.S. Pat. No. 4,430,653, Feb. 7, 1984.

Davis, J. L., Rossiter, J. R., Mesher, D. E., and Dawley, C. B., 1994. Quantitative Measurement Of Pavement Structures Using Radar. Proceedings of the 5th Annual Conference on Ground Penetrating Radar, June 12–16, Kitchener, Ontario, Canada, pp. 319–334.

Fowler, J. C., L. A. Rubin, and W. L. Still. Synthetic Pulse Radar including a Microprocessor Based Controller. Ensco, Inc., U.S. Pat. No. 4,218,678, Aug. 19, 1980.

Goodman, D. "Ground-Penetrating Radar Simulation In Engineering And Archaeology," *Geophysics*, Vol. 59, No. 2, February, 1994, pp. 224–232.

*GSSI High Speed Radar Pavement Structure Evaluation System*. SIR-10H Data Acquisition Control Unit. Brochure, Geophysical Survey System, Inc., North Salem, N.H., Oct. 30, 1995.

Grigas, J. *Microwave Dielectric Spectroscopy of Ferroelectrics and Related Materials*. Gordon & Breach Publishers, Inc. 1996.

Han, H. C., and C. S. Wang, Microwave Imaging In Inhomogeneous Materials, *Proc. Prog. In Electromag. Res. Sym.*, July 24,28, Seattle, Wash., 1995.

Han, H. C., and C. S. Wang, Coherent microwave imaging for buried objects, *Review in Progress in Quantitative Nondestructive Evaluation*, 14, 607–613, Plenum, New York, 1995.

Han, H. C., and C. S. Wang, Microwave imaging in inhomogeneous media, *Advanced Microwave and Millimeter Wave Detectors*, Eds. Udpa and Han, Proc. SPIE 2275, 226–230, 1994.

Imai, Tsuneo, T. Sakayama, and T. Kanemori. "Use Of Ground-Probing Radar And Resistivity Surveys For Archaeological Investigations," *Geophysics*, Vol. 52, No. 2, February 1987, pp. 137–150.

Kaufman, A. A., and J. D. McNeill. Signal Processing Apparatus for Frequency Domain Geophysical Electromagnetic Surveying System. Geonics Limited, U.S. Pat. No. 4,544,892, Oct. 1, 1985.

Khan, R. B. Gamberg, D. Power, J. Walsh, B. Dawe, W. Pearson, and D. Millan. Taret Detection And Tracking With A High Frequency Ground Wave Radar. *IEEE Journal of Oceanic Engineering* 19(4), October 1994, 540–548.

Kovas, J. E. Survey Applications Of Ground-Penetrating Radar. *Surveying and Land Information Systems* 51(3), 1991, 144–148.

Lytton, R. L. (1995a) System Identification and Analysis of Subsurface Radar Signals. The Texas A&M University System, U.S. Pat. No. 5,384,715, Jan. 24, 1995.

Parra, J. O., T. E. Own, and B. M. Duff. Method and Apparatus for Detecting Subsurface Anomalies. Southwest Research Institute, U.S. Pat. No. 4,835,474, May 30, 1989.

Roberts, F. L., P. S. Kandhal, E. R. Brown, D. Y. Lee, and T. W. Kennedy. *Hot Mix Asphalt Materials, Mixture Design, and Construction*. NAPA Research and Education Foundation. March 1994.

Schroeder, D. Method and Apparatus for Detecting and Measuring Inclusions in Subsoil. U.S. Pat. No. 4,245,191, Jan. 1, 1981.

Thomas, B. J. Method for Using Seismic Data Acquisition Technology for Acquisition of Ground Penetrating Radar Data. Conoco Inc., U.S. Pat. No. 5,113,192, May 12, 1992.

Troxler 3430 Road/Reader Brochure. Troxler Electronic Laboratories, Inc. Research Triangle Park, North Carolina, 1995.

Vaughan, C. J. "Ground-penetrating radar surveys in archaeological investigations," *Geophysics*, Vol. 51, No. 3, March, 1986, pp. 595–604.

Von Hippel, A., editor. *Dielectric Materials and Applications*. Published jointly by The Technology Press of M.I.T. and John Wiley & Sons, New York, 1954, 356.

Measuring density changes of hot mix asphalt pavement throughout the compaction process depends primarily on the physical or chemical properties of the asphalt. Studies have been made to investigate the dielectric properties of asphalt pavements and its constituents. The dielectric properties for several types of organic and inorganic solids, including asphalt, have been determined. Studies have shown that dielectric measurements discriminate between asphalt sources and that dielectric properties are significantly affected by aging. Studies have also found that this method did not discriminate between different asphalts when in the presence of the aggregate since the dielectric constants for the aggregate are approximately one order of magnitude larger than those for the asphalt binders, and therefore the dielectric properties of the aggregate dominate the measured values for the mixes. To date, no research has been performed correlating electromagnetic signals to asphalt pavement density in real time during the compaction process. The present invention develops such correlations as well as tests an innovative density measurement approach that minimizes dependence on the numerous changing parameters of the hot mix asphalt pavement during the rolling process. With the desired correlations developed, the approach of the present invention is faster and more reliable than using conventional GPR techniques, for example.

A need can therefore be seen for a nondestructive fast device that would carefully monitor pavement quality on an in-process, real-time basis. Such a device should measure and simplistically display the parameter that indicates pavement quality; it should also provide feedback to roller operators, enabling them to make corrections during the rolling operation.

Features of the Invention

A general feature of the present invention is the provision of a method and apparatus for sensing asphalt pavement quality in real time which overcomes problems found in the prior art.

A further feature of the present invention is the provision of a method and apparatus for sensing asphalt pavement quality in real time using a differential approach during the asphalt rolling operation.

Further features, objects and advantages of the present invention include:

A method and apparatus for sensing asphalt pavement quality in real time using dual microwave signal sensors.

A method and apparatus for sensing asphalt pavement quality in real time using dual continuous wave sensors.

A method and apparatus for sensing asphalt pavement quality in real time using dual ground penetrating radar sensors.

A method and apparatus for sensing asphalt pavement quality in real time using dual nuclear gauge sensors.

A method and apparatus for sensing asphalt pavement quality in real time using dual capacitance energy dissipation (CED) devices.

A method and apparatus for sensing asphalt pavement quality in real time using dual laser acoustic sensors.

A method and apparatus for sensing asphalt pavement quality in real time which uses dual sensors and monitors the difference in the variance between the two sensors.

A method and apparatus for sensing asphalt pavement quality in real time which can be used without knowing the temperature, binder type, and aggregate type used in the asphalt.

A method and apparatus for sensing asphalt pavement quality in real time capable of determining the asphalt density in real time during the compaction process.

A method and apparatus for sensing asphalt pavement quality in real time which makes no contact with the surface of the asphalt.

A method and apparatus for sensing asphalt pavement quality in real time which is faster and more reliable than existing density measurement techniques.

A method and apparatus for sensing asphalt pavement quality in real time which provides benefits such as reduced construction and maintenance costs, improved pavement quality, faster paving times, and increased safety of motorists on asphalt roads and highways.

A method and apparatus involving an asphalt pavement quality sensor for real-time control of paving density which minimizes the frequent disparities between contractor field lab results and agency lab results.

These as well as other features, objects and advantages of the present invention will become apparent from the following specification and claims.

SUMMARY OF THE INVENTION

An apparatus and method for determining in real time the density of a material on a ground surface during a rolling operation is used to determine when the optimal level of compaction has been achieved. The invention is comprised of a pair of sensors disposed in front of the roller and behind the roller. By monitoring information from the two sensors, the density of the material being compacted can be determined.

In one example, the present invention is comprised of two sensors which each receive a reflected microwave signal from an asphalt mat and analyze the reflected signals to determine when the optimal level of compaction has been reached. Preferably, the variance in the reflected microwave signal is compared over successive passes with the roller to help determine when the optimal level of compaction has been reached.

DETAILED DESCRIPTION OF THE PREFERRED EMBODIMENT

The present invention will be described as it applies to its preferred embodiment. It is not intended that the present invention be limited to the described embodiment. It is intended that the invention cover all alternatives, modifications, and equivalencies which may be included within the spirit and scope of the invention.

To address the limitations of the existing systems for asphalt pavement density measurement, the present invention has been developed as a new approach to measuring asphalt quality in real time. The approach involves the development of a system using dual sensors during the asphalt rolling operation. In the preferred embodiment, the system uses dual microwave signal sensors. From a practical point of view, the unique advantage of the present invention is the ability of a roller operator to monitor the density of asphalt during the rolling process, creating several benefits that have not been possible using existing sensing techniques which use a single sensor.

The approach taken by the present invention allows certain parameters to be excluded because a comparison technique is being used. Thus, it is possible to eliminate unknown pavement characteristics (such as temperature, the binder, etc.) that might affect the accuracy of prior art approaches. The sensor of the present invention uses a microwave technique that is based on the continuous comparison of microwave signals reflected off the asphalt pavement.

The present invention uses a statistical approach to relate measurements from an asphalt layer to its compaction level. Field experiments (described below) have been conducted on asphalt strips of different compaction levels to verify the operation of the present invention. These field experiments were conducted using microwave sensors, although various other sensors could also be used. In these experiments, X-band microwave sensors were used to collect the reflection data. The variabilities in the microwave reflection from different strips were analyzed. A definite correlation between the variability and the number of roller passes can be observed. This correlation is further attributed to the scattering processes caused by the rough asphalt surface, air voids, and the random inhomogeneities in the asphalt layer (illustrated in FIG. 4).

Following is an overview of the physical background of the concepts relied upon by the present invention. The physical background will be discussed in the context of the preferred embodiment (microwave signals), although it should be understood that there are-various alternative sensors that can be used with the present invention.

The average amplitude and phase of the reflection coefficient are functions of the complex effective permittivity of the asphalt mixture. In general, the effective permittivity, $\epsilon_{\mathit{eff}}=\epsilon'-j\epsilon''$, of a material with embedded random inhomogeneities affects how microwaves propagate and are attenuated in that material. In this case, the real part, $\epsilon'$, of the asphalt's complex permittivity can be related to the polarization of the pavement in the microwave field. The real part $\epsilon'$ varies with the pavement composition (e.g., mix design, aggregate gradation, and density). The imaginary part, $\epsilon''$, describes the losses, i.e., the absorption and scattering of microwaves in the pavement.

The effective propagation constant of a plane microwave in asphalt is given by $$\gamma = k_0 \epsilon^{1/2}_{\mathit{eff}} \quad [1]$$

where $k_0$ is the free space wavenumber, which can be related to the wavelength of the microwave, $\lambda_0$, through the relationship $k_0 = 2\pi/\lambda_0$. The reflection coefficient for a microwave normally incident from free space on an infinite slab of asphalt of thickness, d, is given by $$R = \frac{R_i + R_j \exp(-2i\gamma d)}{1 + R_i R_j \exp(-2i\gamma d)} \quad [2]$$

where $$R_i = \{k_0 - \gamma\}/\{k_0 + \gamma\} \quad [3]$$

is the Fresnel reflection coefficient for the air-asphalt interface, and $R_j$ is the Fresnel reflection coefficient between the asphalt layer and the subbase. Thus, the reflection coefficient given by Equation [2] is a function of $\epsilon'$, $\epsilon''$, the thickness of the mat, d, and frequency, $\omega$, or wavelength, $\lambda_0$.

The sensitivity of $\epsilon_{\mathit{eff}}$ to air voids or density of asphalt pavement causes the reflection coefficient to change. This change can be detected in the reflected signal and used to determine the asphalt pavement density. However, other parameters that do not have direct relation with asphalt density could also cause the reflection coefficient to change. For example, variations in the thickness of the asphalt mat, or changes in subbase characteristics will alter the values of d, and $R_j$, respectively, in Equation (2), hence modify the reflected microwave signals. Therefore, we employ an approach to process the microwave reflection signals such that the effects of parameters that have no associations with asphalt density can be kept at a minimum.

The present invention can be implemented using a variety of sensors. Following are various examples of sensor types that could be used with the present invention including: continuous wave (CW) sensors, capacitance energy dissipation (CED) devices, ground penetrating radar (GPR), nuclear gauges, ultra sound devices, laser acoustic sensors, etc. Of course, other types of sensing or analization equipment may also be used.

Figure 1:
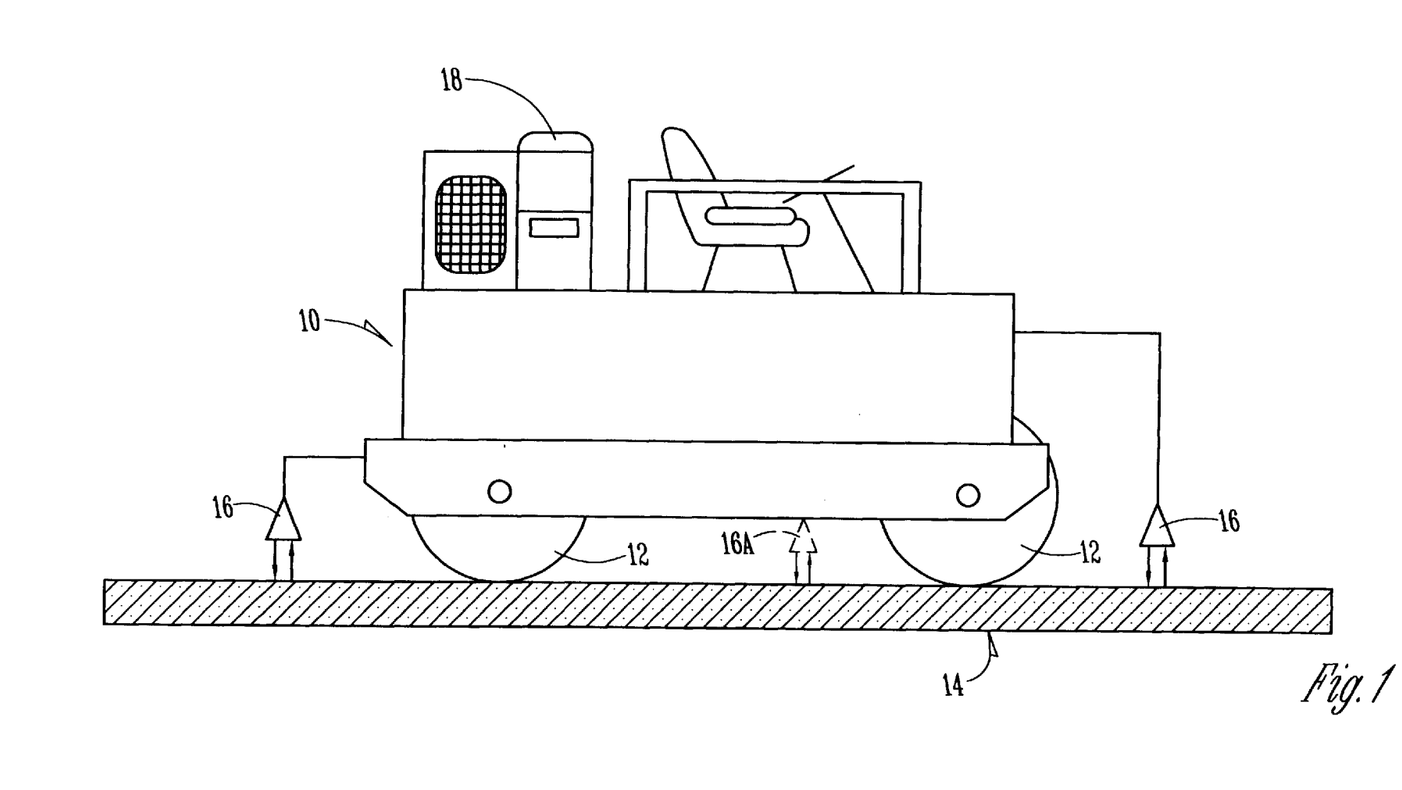
FIG. 1 is a view of a real time asphalt pavement quality sensor attached to a vibratory roller.

In the preferred embodiment, continuous wave sensors, such as microwave sensors, are used with the present invention. FIG. 1 shows a vibratory roller 10 having front and rear steel rollers 12 for compacting and flattening a mat of asphalt pavement 14. While the present invention is described for use with a vibratory roller, any other type of roller could also be used. In addition, for the purposes of this description, the terms "front" and "back" with respect to the roller 10 are relative since a roller 10 operates in either direction. Therefore phrases such as "the front of the roller" could refer to either end of the roller 10 depending on the direction of travel.

The roller 10 includes two sensors 16 (in the preferred embodiment, two antennas 16), one in front of the roller 10 and one behind it. FIG. 1 also shows an alternative location of one of the sensors. As shown, an alternate sensor 16A is located behind one of the rollers 12. FIG. 1 also shows a microwave signal generator and processor 18 located on the roller 10. The antennas 16 are used to transmit and receive microwave signals (represented in FIG. 1 by two arrows), which are processed by the processor to continuously measure the level of imbalance between the two reflected microwave signals. This imbalance shows the roller operator, in real time, the difference in pavement density in front of and behind the roller for specific pavement conditions. It is important to remember that the temperature, binder, and other variables are the same at each antenna, so that the only variable is the level of compaction. A given value of this signal difference will show the optimum compaction and density of asphalt pavement. By using microwave signals of the proper frequency, preferably in the range of 8 to 30 GHz, the influence of a large number of other parameters that affect the reflectivity of pavement will be minimized.

Figure 2:
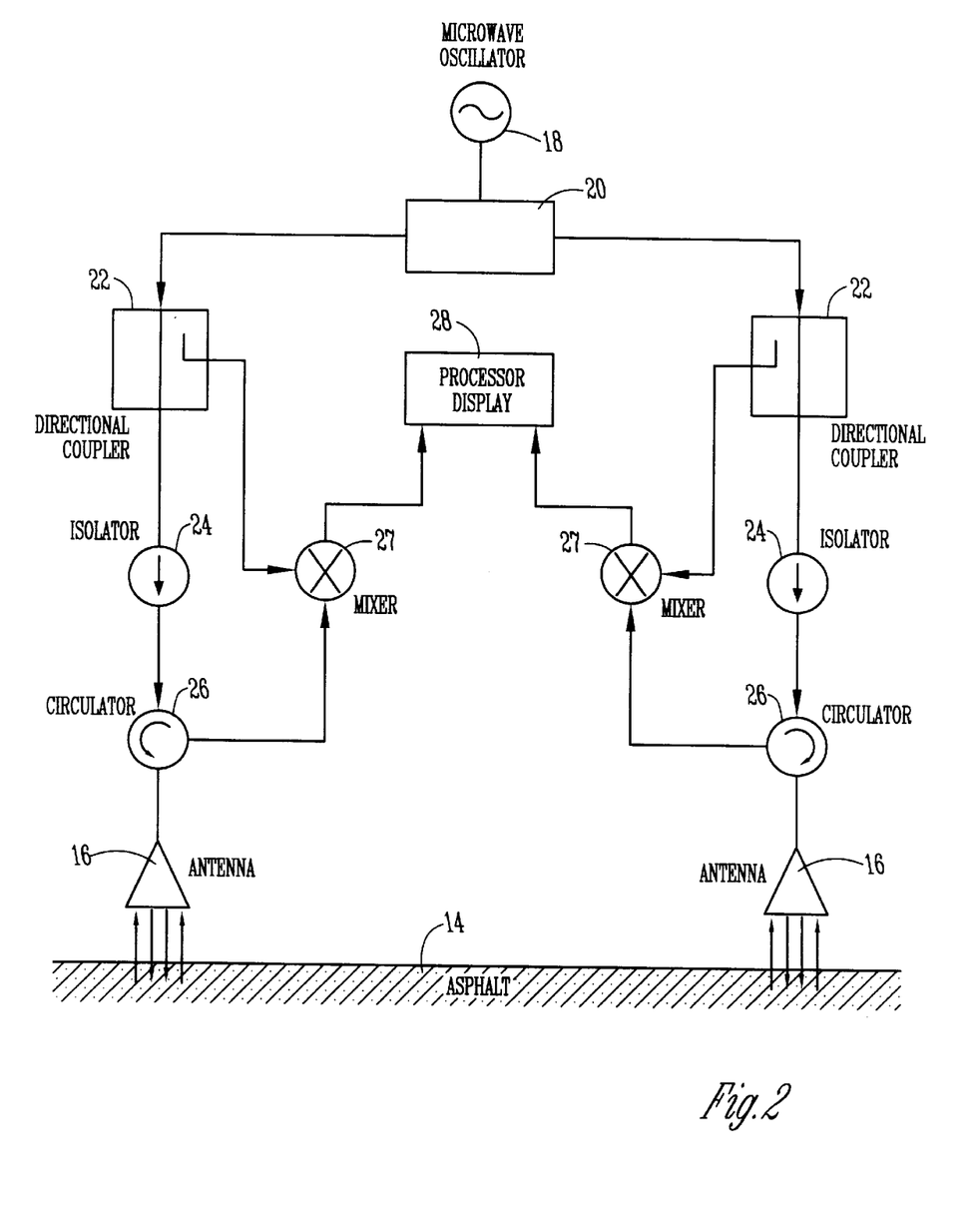
FIG. 2 is a block diagram of one embodiment of a real time microwave pavement sensor of the present invention.

FIG. 2 is a block diagram of the microwave pavement sensor shown in FIG. 1. Again, the embodiment shown in FIGS. 1 and 2 is only one example of many possible embodiments. As shown, a microwave source 18 transmits a microwave signal to a power splitter 20. The microwave source 18 is preferably comprised of a low-power microwave oscillator. The power splitter 20 transmits the microwave signal via two sets of directional couplers 22, isolators 24, and circulators 26 to the horn antennas 16 which are pointed substantially perpendicular to the asphalt pavement 14.

The present invention is implemented by placing one antenna 16 in front of the roller 10 and the other antenna 16 behind the roller 10. The antennas 16 each transmit the microwave signal toward the pavement 14 and pick up the reflected signals (represented in this description as $R_1$ and $R_2$). The reflected signals $R_1$ and $R_2$ carry information about the pavement parameters (i.e., dielectric permittivity that depends on the pavement density). The reflected signals $R_1$ and $R_2$ are propagated through the two corresponding sets of circulators 26 and mixers 27, where the carrier frequency is removed, to the signal processor 28, where the statistics and variability of each of $R_1$ and $R_2$ are computed and compared.

Figures 3, 4:
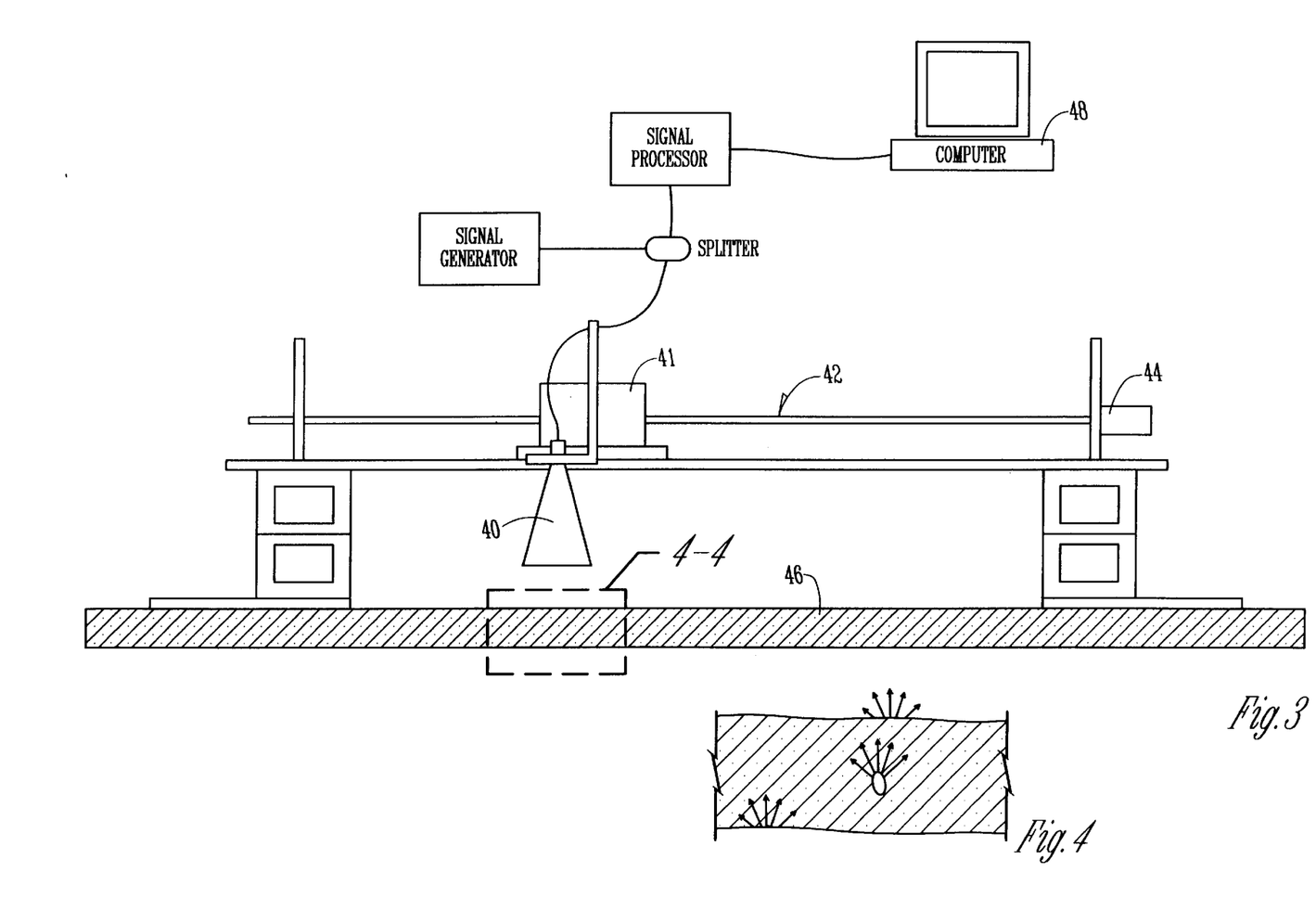
FIG. 3 is a diagram showing a testing apparatus for one embodiment of the present invention using microwaves.
FIG. 4 is a sectional view of an asphalt mat showing the effects of scattering.
Figures 5A, 5B:
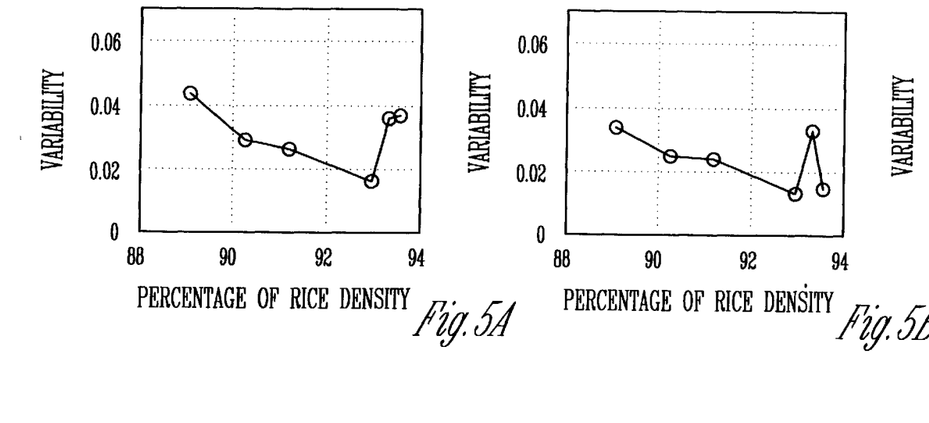
FIGS. 5A–5K illustrates charts showing the variability versus percentage of rice density over various numbers of roller passes at various frequencies.
Figure 5C:
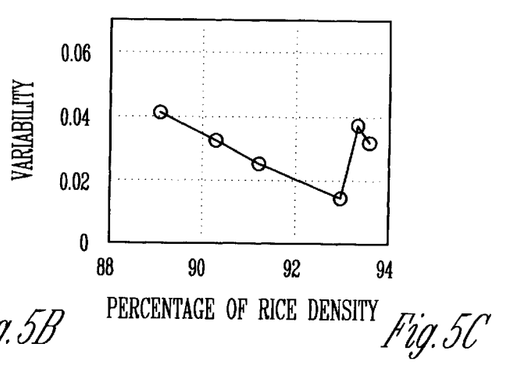
Figures 5D, 5E:
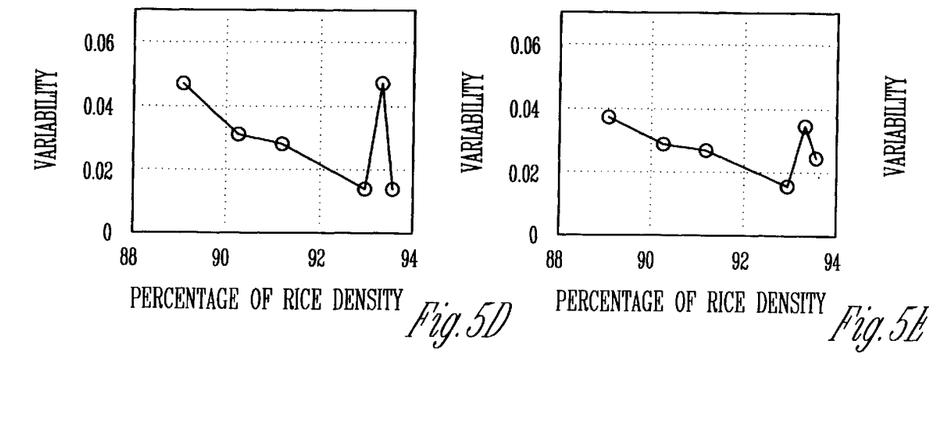
Figure 5F:
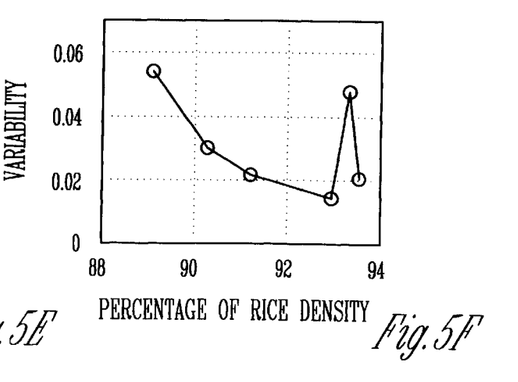
Figures 5G, 5H, 5I:
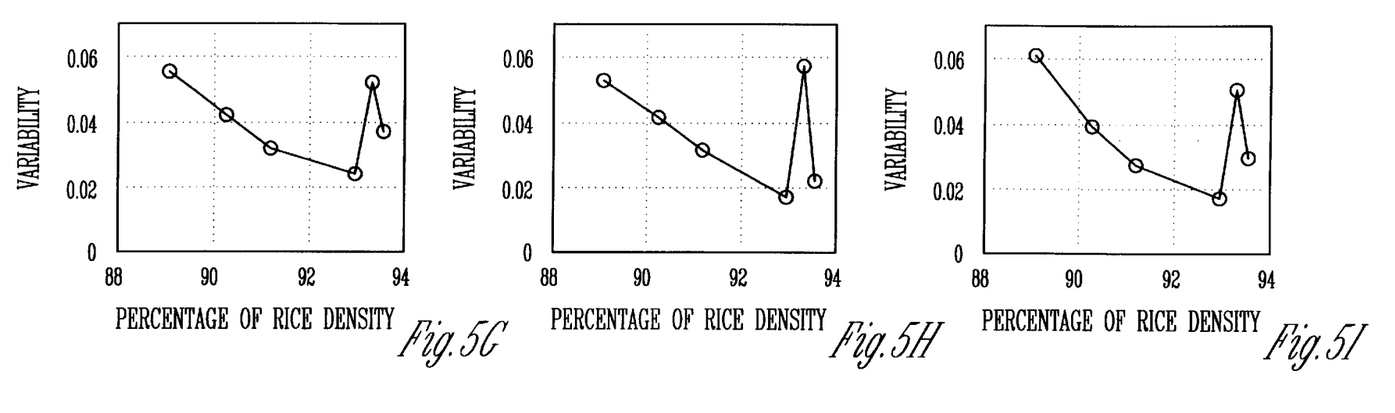
Figures 5J, 5K:
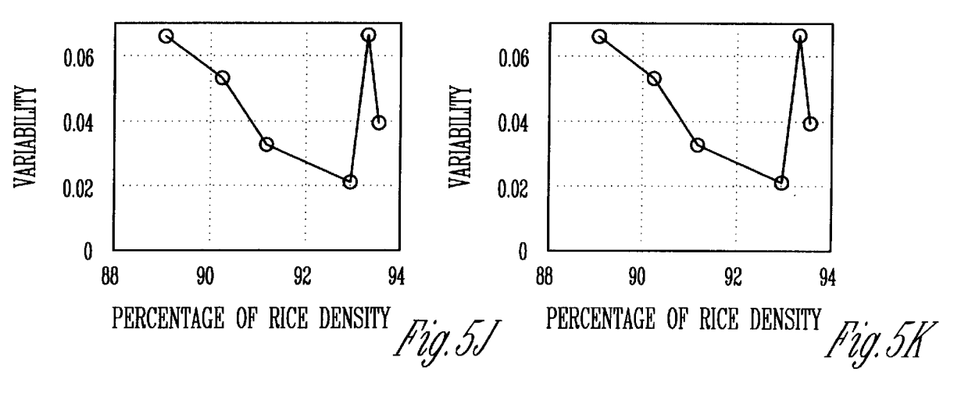

In the preferred embodiment, a stochastic approach to comparing $R_1$ and $R_2$ is employed in the system design. Probabilistic distributions of each reflection coefficient are developed, and a statistical test is performed to determine the statistical difference between the variabilities of each distribution. The variability of microwave reflection signals characterizes the uniformity of the asphalt pavement internal makeup, the surface condition, and the subsurface condition (FIG. 4). As roller compacting causes the asphalt density to increase, the aggregate and air void distributions inside the asphalt mat as well as the top (asphalt-air interface) and bottom (asphalt-subbase interface) rough surface conditions become more uniform along the asphalt strip. Therefore, the variability of microwave reflection signals will decrease as a result of roller compaction.

Before the optimal compaction is reached, the formation of aggregate interlocks (or, stone-on-stone contacts) will take place. This phenomenon constitutes a change in physical configuration of the asphalt internal makeup that will locally modify the microwave reflection signals. At the onset of optimal compaction, such areas of interlocked aggregate sparsely scatter along the asphalt strip, and the sporadically modified microwave signals lead to an increase in the overall variability. As the roller compaction continues and the interlocked aggregate becomes a commonplace feature of the entire asphalt strip, the variability drops again (see supporting data).

Therefore, the changes in the variability of microwave reflection signals can be used as a qualitative indicator of asphalt density and is less susceptive to the influences of other factors (e.g., asphalt mat thickness, subbase condition) that have little to do with asphalt density but may have direct effects on the values of microwave reflection coefficients.

A reliable system can be realized using a differential approach. In this case, the histograms of $R_1$ and $R_2$ are generated every three to five seconds along with the variability of each distribution.

The variability of the distribution of each of the two reflection signals $R_1$ and $R_2$ can be quantified with the following formula:

$$\sigma^2 = \sum_{n=1}^{N} \frac{|c_n - \bar{c}|^2}{N-1}$$

where N is the total number of measurements taken during each three to five second interval, $c_n$ is the complex microwave reflection signal ($R_1$ and $R_2$) recorded at the n-th measurement point, and $\bar{c}$ is the average complex microwave reflection signal. When the difference between the two variabilities is larger than a set target value, then the asphalt pavement density is at its optimal point and the compaction portion of the rolling operation is finished. This technique provides reliable results.

FIG. 3 shows an apparatus for field testing the preferred embodiment of the present invention on test strips of asphalt pavement. First, a number of strips of asphalt were paved and rolled a different number of times (therefore each having different densities). Additionally, both hot mix and core samples were taken from the strips to determine the actual density of each asphalt mat. This arrangement enabled measurements to be taken from strips of asphalt that had undergone several levels of compaction. The electronic equipment used for the testing consisted of the following: a Hewlett Packard (HP) 8350B sweep oscillator, an HP 8410A network analyzer, an HP 8411A harmonic frequency converter, an Apex personal computer, a motor-driven linear positioner, a Narda Model 640 standard gain horn antenna, and other components such as isolators, directional couplers, waveguides, and cables.

As shown in FIG. 3, an antenna 40 and linear scanner 41 are mounted on a motor-driven positioner 42 driven by a stepper motor 44 to obtain measurements at multiple locations along a particular strip of asphalt 46. A measurement set began with the sweep oscillator generating signals from 8 GHz to 12 GHz in increments of 0.4 GHz. The values for the reflected signals at these frequencies were stored in a data set on the hard drive of computer 48. The positioner 42 then moved the antenna 40 forward by 2 cm and the next data set was obtained. This procedure was repeated until 40 data sets were taken. In other words, each measurement set contained 40 data sets, with each data set containing data from the above-mentioned 11 different frequencies. A variety of measurement sets was taken using three different antenna positions (10 cm, 12.5 cm, and 15 cm above the asphalt surface) and two separate angles of incidence (0° and 10°). Experiments were performed while the asphalt was hot, then a few hours after paving, and finally one day after the paving was completed. In all, over 80 measurement sets were obtained. This collection of measurement sets has enabled a preliminary analysis of the best parameters to use during a more comprehensive field test.

Figure 6:
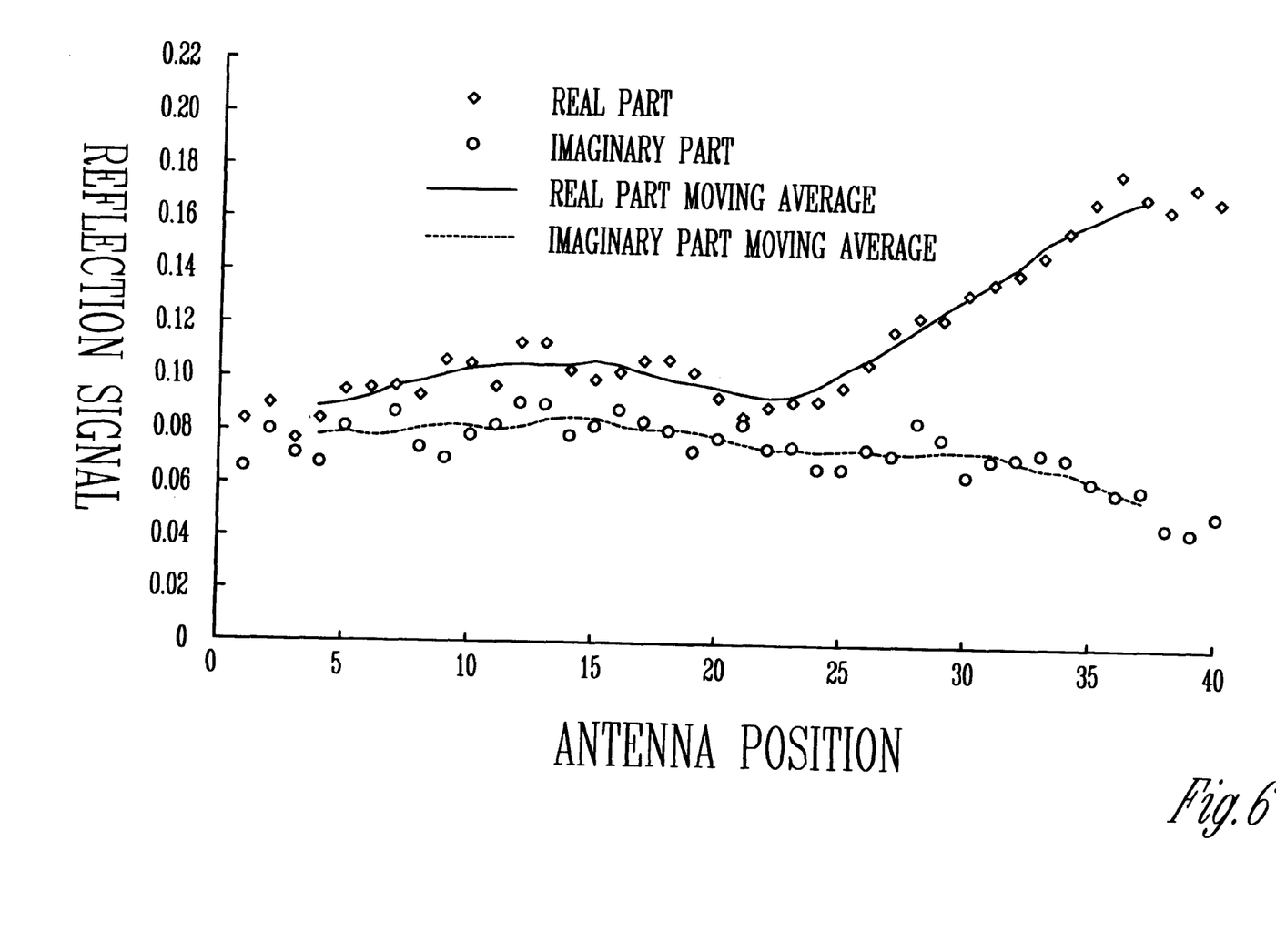
FIG. 6 is a graph showing the reflected signal versus antenna position taken from the testing equipment shown in FIG. 3.
Figure 7A:
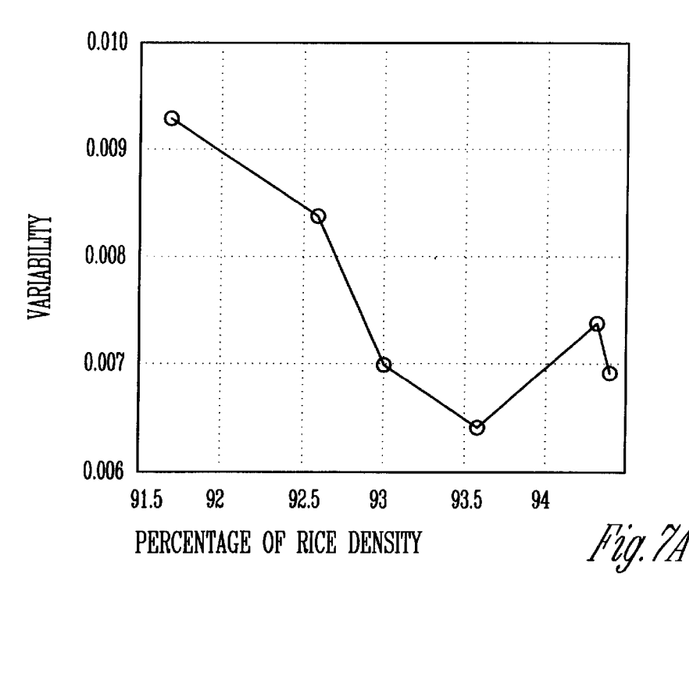
FIGS. 7A and 7B are charts showing the variability versus percentage of Rice density after various roller passes.
Figure 7B:
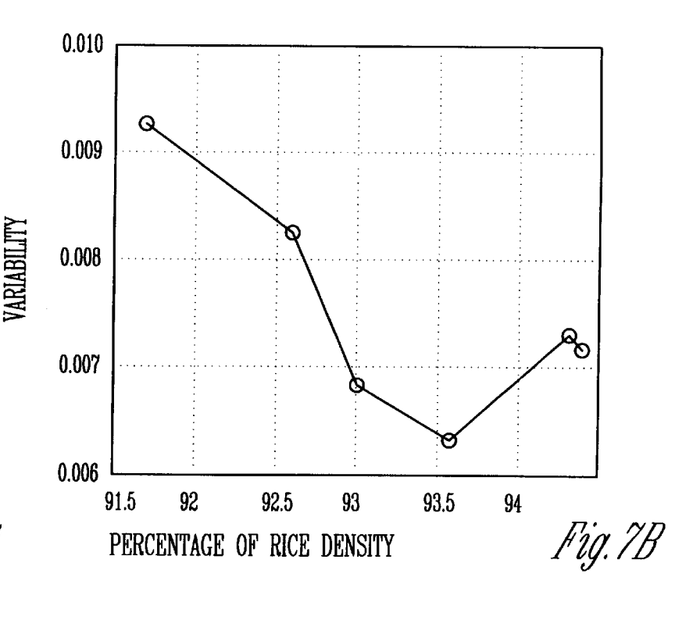

FIGS. 5–7 show data from the testing that is representative of all of the data from the testing. FIGS. 5A–5K show the variability versus percentage of Rice density for hot asphalt mats prepared during a first field testing with the antenna 40 (FIG. 3) at 15 cm above the asphalt 46 and at frequencies of 8.0 GHz, 8.4 GHz, 8.8 GHz, 9.2 GHz, 9.6 GHz, 10.0 GHz, 10.4 GHz, 10.8 GHz, 11.2 GHz, 11.6 GHz, 12.0 GHz, respectively. In FIGS. 5A–5K, each circle on the charts represents the variability at 2, 4, 6, 8, 10, and 12 roller coverages (from left to right). FIG. 6 is a chart of the calibrated value from the signal received by the antenna 40 in a second field testing at the various antenna positions on a hot test strip of asphalt. The solid lines in FIG. 6 result from "data smoothing". Each point on the solid line represents an average of the seven data points nearest that point on the line. For example, the start of the solid line shown is at antenna position 4 and is an average of the data at antenna positions 1–7. Then, the variance of the original data with respect to the moving average is calculated for the graph shown in FIGS. 7A and 7B. FIGS. 7A and 7B show two charts of the variability versus the percentage of Rice density for a number of roller passes at a frequency of 8 GHz, where each circle on the charts corresponds to a roller pass. FIG. 7A shows a forward scan and FIG. 7B shows a backward scan. The system shown in FIGS. 1 and 2 therefore compares the variances of the front and back antennas 16 (since the asphalt behind the roller 10 is one coverage ahead of the asphalt in front of the roller 10) to determine the when the optimal level of compaction has been reached.

As shown in the charts of FIG. 5, the variability was found to decrease as the number of roller coverages increased from two to eight (the first four circles in each of FIGS. 5A–5K). The graphs shown in FIG. 5 depict how the variability decreased as the corresponding asphalt density increased, yet shows a discontinuity after the eighth coverage (the eighth coverage corresponds to the fourth circle in each chart).

When the asphalt used in this study was covered over eight times with this particular roller, optimal compaction was achieved. This is the state in which the aggregate within the asphalt begins to form "stone-on-stone" contacts. The jump in variability occurring after eight coverages can be attributed to the consequential change of microwave scattering mechanism, as described previously. This jump, or spike, shown in FIG. 5 therefore occurs at a point where the compaction process can be safely stopped. In practice, the determination of when optimal compaction is reached could be achieved in many ways. Since measurements are continuously taken during each coverage of the roller, some measurements will show a "spike" while others may not. In one example, the spikes could be counted during each pass and the count used to determine when to stop roller. For example, optimal compaction may be determined to be reached once a certain percentage of the measurements results in a "spike".

The variation in the magnitude of the spikes shown in FIGS. 5A–5K may be explained as follows. As shown in FIGS. 5A–5K, the magnitude of the spikes are different for different frequencies. When the thickness of the asphalt layer, d, is equal to $n\lambda/2$ where n=1,2,3... and $\lambda$ is the wavelength of microwaves in asphalt, the maximum reflection and variability occurs. Therefore, the sensitivity could be increased with the proper choice of frequency.

It is important to realize that with prior art methods of determining asphalt density, the actual density is measured. With the present invention, a more qualitative approach is taken. With the present invention, the difference between the variance in the front and back of the roller 10 is compared, rather than measuring the actual densities. Therefore, the present invention does not require the extended calibration procedures that are essential for prior art methods to correct for errors caused by temperature variation, differences among mix designs, etc.

In another embodiment, capacitance energy dissipation (CED) devices may be used as sensors with the present invention. It has been an established practice to determine the dielectric properties of material using capacitance measurements. For asphalt density measurement, TransTech Systems, Inc. has developed a capacitance energy dissipation (CED) device which measures electrical impedance to provide density and moisture content readings based on a contacting, but noninstrusive and nonradioactive detection technique. The present invention optionally can be implemented with two CED devices, one disposed in front of the roller, the other behind the roller. By monitoring and comparing the electrical impedance of asphalt measured by the two CED devices either in a direct or statistical manner, one can identify when the optimal compaction of asphalt pavement is reached.

In another embodiment, ground penetrating radar (GPR) devices may be used as sensors with the present invention. Ground penetrating radars use microwave impulses of frequency generally below 2 GHz to probe the construction of subsurface structures. The magnitude and polarity of the return impulses reflected by subsurface interfaces can be used to determine the contrast of electrical permittivities between two adjacent layers. The time delays of the return impulses are used to determine the thickness of each subsurface layer. The present invention optionally can be implemented with two GPRs, one disposed in front of the roller, the other behind the roller. By monitoring and comparing the return impulses received by the two GPR, one can identify when the optimal compaction of asphalt pavement is reached.

In another embodiment, nuclear density gauges may be used as sensors with the present invention. Nuclear density gauges use backscattering count of gamma radiation to determine the density of asphalt mats. Various sensor arrangements and signal processing algorithms have been used by different manufacturers to provide static (stationary) or dynamic (on-the-run) operational capabilities and for full-depth or thin overlay density measurements. In general, nuclear gauges require continuous integration of backscattering counts during a pre-specified measurement period to achieve reliable density readings. Consequently, for dynamic gauges, only averaged density readings over the length of asphalt mat that is covered during a measurement period can be obtained. For thin overlay density measurements the density of the base material and the thickness of the overlay have to be entered into the nuclear gauge. Arrangements with multiple sensors having different relative distances to the asphalt mat surface can also be made to provide thin overlay density measurement without prior knowledge of the density of the underlying base material, such as the two-detector configuration employed in the Troxler 4640 Thin Layer Density Gauge. The present invention optionally can be implemented with two dynamic nuclear density gauges, one disposed in front of the roller, the other behind the roller. By monitoring and comparing the density readings of the two nuclear gauges, one can identify when the optimal compaction of asphalt pavement is reached.

In another embodiment, laser acoustic sensors may be used as sensors with the present invention. Laser acoustic sensors may be used to measure the mechanical vibration of the asphalt pavement produced by a vibratory roller. In general, asphalt mats of different densities resonate with mechanical vibration differently. The change in frequency response of asphalt to mechanical vibration caused by a change in pavement density can be used to probe the compaction level of asphalt. One possibility is to use laser inferometers to measure the amplitude and frequency of vibration on the asphalt surface in real time. With one such sensor placed in front of the roller and one placed behind the roller, a user can compare the changes in the signatures of vibration data and identify when the optimal compaction of asphalt pavement is reached. If this type of sensor is used with the present invention, it is believed that the alternate location of the sensors 16 and 16A (FIG. 1) would be preferred since variations (as seen by the sensors) in the vibration of the asphalt mat 14 caused by the roller 10 would be reduced.

While the present invention preferably uses microwave sensors or any of the above mentioned systems, the concept of dual sensors could be applied using any number of other types of systems by using such a sensor at both ends of a roller so that a comparison of the readings from the sensors can be used. Other optional alternatives which could be used with the present invention include the use of compressed air to blow water or debris away from the asphalt surface before taking readings and the use of mechanical or electronic means to remove the effect of vibratory noise produced by breakdown rollers. It is possible that water, debris, or vibrational movement could affect the readings of a microwave (or other) sensors. In another alternative embodiment, the system could be implemented with a GPS or other navigational device to correlate locations on the asphalt with measurements at those locations.

The present invention could also be used in applications other than the compaction of asphalt pavement. For example, when preparing the subbase of a road or parking lot, the present invention could be used to check soil compaction of the subbase.

The development of the present invention opens up a range of new applications, which have not been feasible with available ground-penetrating radar (GPR) or other sensors due to their inherent limitations. The innovation of the present invention provides faster, more reliable continuous assessment of pavement quality than current techniques, minimizing the frequent disparity between contractor lab results and transportation agency lab results.

The preferred embodiment of the present invention has been set forth in the drawings and specification, and although specific terms are employed, these are used in a generic or descriptive sense only and are not used for purposes of limitation. Changes in the form and proportion of parts as well as in the substitution of equivalents are contemplated as circumstances may suggest or render expedient without departing from the spirit and scope of the invention as further defined in the following claims.

What is claimed is:

1. A method of determining when the optimal level of compaction of asphalt pavement has been achieved comprising the steps of:

compacting the asphalt pavement with a roller;

sensing a first property of the asphalt in front of the roller;

sensing the first property of the asphalt behind the roller;

determining the variance of the sensed property in front of the roller and the variance of the sensed property behind the roller; and monitoring the determined variance of the sensed property in front of the roller and the determined variance of the sensed property behind the roller to determine whether the optimal level of compaction has been achieved.

2. The method of claim 1 further comprising the step of comparing the determined variance of the sensed property in front of the roller and the determined variance of the sensed property behind the roller to determine when the variance has increased.

3. The method of claim 1 further comprising the steps of: comparing the determined variance of the sensed property in front of the roller and the determined variance of the sensed property behind the roller to determine when the variance has spiked.

4. An apparatus for determining in real time the density of a material on a ground surface during a rolling operation comprising:

a roller for compacting material on the ground surface;

a first microwave antenna disposed in front of the roller;

a second microwave antenna disposed behind the roller; and a processor electrically connected to the first and second microwave antennas for generating data relating to the density of the material based on information from the first and second microwave antennas.

5. The apparatus of claim 4 wherein the microwave antennas transmit microwave signals toward the ground surface and receive reflected microwave signals from the ground surface.

6. The apparatus of claim 5 further comprising a detector for determining the difference between the reflected signals from the first sensor and the reflected signals from the second sensor.

7. The apparatus of claim 4 wherein the material is asphalt pavement.

8. The apparatus of claim 7 wherein the processor performs the processing steps of:

determining the variance of the signals received by the first sensor and determining the variance of the signals received by the second sensor; and determining whether the asphalt pavement is compacted to a desired level based on the determined variances.

9. The apparatus of claim 8 wherein the asphalt pavement is determined to be compacted to a desired level when the determined variance of the second sensor is greater than the determined variance of the first sensor.

10. A method of determining in real time when the optimal level of compaction of asphalt pavement has been reached comprising the steps of:

compacting the hot asphalt pavement by traveling over the asphalt pavement with a roller;

successively sensing a property of the asphalt related to density in front of the roller;

successively sensing a property of the asphalt related to density behind the roller;

determining the difference between the sensed property of the asphalt in front of the roller and the sensed property of the asphalt behind the roller; and using the differences between the sensed properties to determine whether the optimal level of compaction has been achieved.

11. A method of determining the density of material on a ground surface while operating a rolling device comprising the steps of:

sensing information in front of the rolling device using a microwave sensor;

sensing information behind the rolling device using a microwave sensor; and comparing the sensed information to determine the density of the material.

12. A method of determining when the optimal level of compaction of asphalt pavement has been achieved comprising the steps of:

compacting the asphalt pavement with a roller;

sensing a first property of the asphalt in front of the roller using microwave signals;

sensing the first property of the asphalt behind the roller using microwave signals; and using the sensed properties to determine whether the optimal level of compaction has been achieved.

13. The method of claim 12 wherein the microwave signals are directed toward the asphalt and reflected microwave signals are received to determine information about the density of the asphalt.

14. The method of claim 13 wherein the reflected microwave signals received in front of the roller and behind the roller are compared to determine information about the first property of the asphalt.

15. The method of claim 12 wherein the first property of the asphalt is density.

16. A method of determining in real time when the optimal level of compaction of asphalt pavement has been reached comprising the steps of:

compacting the hot asphalt pavement by traveling over the asphalt pavement with a roller;

successively sensing a property of the asphalt related to density in front of the roller;

successively sensing a property of the asphalt related to density behind the roller;

determining the variance of the sensed property of the asphalt in front of the roller and the variance of the sensed property of the asphalt behind the roller; and using the variances of the sensed properties to determine whether the optimal level of compaction has been achieved.

17. The method of claim 16 further comprising the step of determining when the optimal level of compaction of asphalt pavement has been reached by monitoring the determined variances.

18. The method of claim 17 further comprising the step of stopping the compacting step when the difference between the determined variances indicates a spike in the magnitude of the variances over successive passes of the roller.

* * * * *